United States Patent
O'Hagan et al.

(10) Patent No.: US 9,669,118 B2
(45) Date of Patent: Jun. 6, 2017

(54) METHOD OF LABELLING A BIOLOGICALLY ACTIVE MOLECULE WITH 5-FLUORO-5-DEOXYPENTOSE OR A 3-FLUORO-3-DEOXYPENTOSE

(75) Inventors: David O'Hagan, Fife (GB); Xiang-Guo Li, Turun Yliopisto (FI)

(73) Assignees: UNIVERSITY COURT OF THE UNIVERSITY OF ST. ANDREWS (GB); TURIN YLIOPISTO (FI)

( * ) Notice: Subject to any disclaimer, the term of this patent is extended or adjusted under 35 U.S.C. 154(b) by 263 days.

(21) Appl. No.: 14/125,978

(22) PCT Filed: Jun. 11, 2012

(86) PCT No.: PCT/GB2012/000505
§ 371 (c)(1),
(2), (4) Date: Apr. 10, 2014

(87) PCT Pub. No.: WO2012/172283
PCT Pub. Date: Dec. 20, 2012

(65) Prior Publication Data
US 2014/0227181 A1 Aug. 14, 2014

(30) Foreign Application Priority Data
Jun. 17, 2011 (GB) .................. 1110239.9

(51) Int. Cl.
A61K 51/00 (2006.01)
A61M 36/14 (2006.01)
A61K 51/04 (2006.01)
A61K 51/08 (2006.01)

(52) U.S. Cl.
CPC .......... *A61K 51/0491* (2013.01); *A61K 51/08* (2013.01); *A61K 51/088* (2013.01)

(58) Field of Classification Search
CPC ............................ A61K 51/0491; A61K 51/08
USPC ....................................................... 424/1.69
See application file for complete search history.

(56) References Cited

U.S. PATENT DOCUMENTS

| 7,040,990 | B2 | 5/2006 | Watanabe et al. |
| 7,294,486 | B2 | 11/2007 | O'Hagan et al. |
| 7,829,032 | B2 | 11/2010 | Van Dam et al. |
| 7,842,279 | B2 | 11/2010 | McBride et al. |
| 8,038,983 | B2 | 10/2011 | McBride et al. |
| 8,211,654 | B2 | 7/2012 | Thorson et al. |
| 2006/0263293 | A1 | 11/2006 | Kolb et al. |
| 2007/0009435 | A1 | 1/2007 | Syud et al. |
| 2010/0029930 | A1 | 2/2010 | Wickstrom et al. |
| 2010/0290988 | A1* | 11/2010 | Cheeseman et al. ........ 424/1.73 |

FOREIGN PATENT DOCUMENTS

| CN | 1775795 A | 5/2006 |
| WO | 0220773 A2 | 3/2002 |
| WO | 03020945 A2 | 3/2003 |
| WO | 03086475 A1 | 10/2003 |
| WO | 2004078914 A2 | 9/2004 |
| WO | 2005028490 A1 | 3/2005 |
| WO | 2005086612 A2 | 9/2005 |
| WO | 2009056837 A2 | 5/2009 |
| WO | 2010133851 A1 | 11/2010 |

OTHER PUBLICATIONS

Grierson et al. J. Labelled Cpd. Radiopharm. 1999, S525-S526.*
International Search Report for Application No. PCT/GB2012/000505 dated Dec. 20, 2012.
International Preliminary Report on Patentability for Application No. PCT/GB2012/000505 dated Dec. 17, 2013.
Search Report for Application No. GB1210194.5 dated Oct. 8, 2012.
Corrected Search Report for Application No. GB1210194.5 dated Oct. 9, 2012.
Search Report for Application No. GB1110239.9 dated Sep. 13, 2011.
Xiang-Guo Li et al.: "(18F)-5-Fluoro-5-Deoxyribose, an Efficient Peptide Bioconjugation Ligand for Positron Emission Tomography (PET) Imaging," Chemical Communications, vol. 48, No. 43, p. 5247-5249, Feb. 20, 2012.
Frank Wuest et al. "Synthesis and Application of 18 F FDG-Maleimidehexyloxime (18 F FDG-MHO): A 18 F FDG-Based Prosthetic Group for the Chemoselective 18 F-Labeling of Peptides and Proteins ," Bioconjugate Chemistry, vol. 19, No. 6, pp. 1202-1210, Jun. 1, 2008.
Frank Wuest et al.: "Direct Labelling of Peptides with 2-(<18>F) Fluoro-2-Deoxy-D-Glucose ([<18>F]FDG)," Bioorganic & Medicinal Chemistry Letters, vol. 19, No. 18, pp. 5426-5428, Sep. 15, 2009.
Mohammad Namavari et al.: "A Novel Method for Direct Site-Specific Radiolabeling of Peptides Using [18F] FDG." Bioconjugate Chemistry, vol. 20, No. 3, pp. 432-436, Mar. 18, 2009.
Mayca Onega et al.: "An Enzymatic Route to 5-Deoxy-5[18F] Fluoro-D-Ribose, a [18F]-Fluorinated Sugar for PET Imaging," Chemical Communications, vol. 46, No. 1, p. 139, Jan. 1, 2010.
O. M. Cociorva et. al.: "Synthesis of Oligosaccharides as Potential Inhibitors of Mycobacterial Arabinosyltransferases. Di- and Trisaccharides Containing C-5 Modified Arabinofuranosyl Residues," Carbohydrate Research, vol. 339, pp. 853-865, 2004.
John A. Wright: "3-Deoxy-3-Fluoro-D-Xylose from Methyl 2,3-Anhydro-B-D-Ribofuranoside," Methods in Carbohydrate Chemistry, vol. 6, pp. 201-205, 1972.
I. Mikhailopulo et. al.: "3'-Fluoro-3'-Deoxyribonucleoside 5'-Triphosphates: Synthesis and Use as Terminators of RNA Biosynthesis," Federation of European Biochemical Societies, vol. 250, No. 2, pp. 139-141, Apr. 17, 1989.
P. W. Kent et. al.: "5-Deoxy-5-Fluoro-D-Xylose, a Crystalline Pentofuranose," Tetrahedron, vol. 27, pp. 4057-4064, 1971.
M. Berndt et. al.: "Labeling of Low-Density Lipoproteins Using the 18F-Labeled Thiol-Reactive Reagent N-[6-(4-[18F] Fluorobenzylidene)Aminooxyhexyl]Maleimide," Nuclear Medicine and Biology, vol. 34, pp. 5-15, 2007.

(Continued)

*Primary Examiner* — Michael G Hartley
*Assistant Examiner* — Sean R Donohue
(74) *Attorney, Agent, or Firm* — J.A. Lindeman & Co., PLLC

(57) ABSTRACT

The invention provides a conjugate of a biologically active molecule and a 5-fluoro-5-deoxypentose or a 3-fluoro-3-deoxypentose, wherein the biologically active molecule is selected from the group consisting of proteins, peptides, nucleic acids, oligosaccharides and polysaccharides.

25 Claims, 4 Drawing Sheets

(56) References Cited

OTHER PUBLICATIONS

O. Boutureira et. al.: "Fluoroglycoproteins: Ready Chemical Site-Selective Incorporation of Fluorosugars into Proteins," Chemical Communications, vol. 41, No. 43, pp. 8142-8144, Nov. 21, 2010.
F. Klepper et. al.: "Synthesis of the Transfer-RNA Nucleoside Queuosine by Using a Chiral Allyl Azide Intermediate," Angewandte Chemie, vol. 46, pp. 2325-2327, 2007.
V. Tolmachev et. al.: "Evaluation of a Maleimido Derivative of NOTA for Site-Specific Labeling of Affibody Molecules," Bioconjugate Chemistry, vol. 22, pp. 894-902, Mar. 29, 2011.
Z. Cheng et. al.: "Small-Animal PET Imaging of Human Epidermal Growth Factor Receptor Type 2 Expression with Site-Specific 18F-Labeled Protein Scaffold Molecules," The Journal of Nuclear Medicine, vol. 49, No. 5, pp. 804-813, Apr. 15, 2008.
C. Dong et. al.: "Crystal Structure and Mechanism of a Bacterial Fluorinating Enzyme," Letters to Nature, vol. 427, pp. 561-565, Feb. 5, 2004.
L. Ducry et. al.: "Antibody—Drug Conjugates: Linking Cytotoxic Payloads to Monoclonal Antibodies," Bioconjugate Chemistry, vol. 21, pp. 5-13, 2010.
R. Egleton et. al.: "Development of Neuropeptide Drugs that Cross the Blood-Brain Barrier," The Journal of the American Society for Experimental NeuroTherapeutics, vol. 2, pp. 44-53, Jan. 2005.
J. Haas, Jr. et. al.: "Rates of Reaction of Nitrogen Bases with Sugars. I. Studies of Aldose Oxime, Semicarbazone and Hydrazone Formation," Journal of American Chemical Society, vol. 84, pp. 4910-4913, Dec. 20, 1962.
D. Harki et. al.: "In Vivo Imaging of Pyrrole-Imidazole Polyamides with Positron Emission Tomography," PNAS, vol. 105, No. 35, pp. 13039-13044, Sep. 2, 2008.
R. Haubner et. al.: "Glycosylated RGD-Containing Peptides: Tracer for Tumor Targeting and Angiogenesis Imaging with Improved Biokinetics," The Journal of Nuclear Medicine, vol. 42, No. 2, pp. 326-336, 2001.
D. Kiesewetter et. al.: "Radiolabeling of HER2-Specific Affibody Molecule with F-18," Journal of Fluorine Chemistry, vol. 129, pp. 799-806, 2008.
J. Lofblom et. al.: "Affibody Molecules: Engineered Proteins for Therapeutic, Diagnostic and Biotechnical Applications," FEBS Letters, vol. 584, pp. 2670-2680, 2010.
F. Sarabia-Garcia et. al.: "Studies on the Synthesis of Tunicamycin. The Preparation of 7-Deoxy-2-Deamino-6-Hydroxy Tunicamine and Related Products," Tetrahedron, vol. 52, No. 13, pp. 4757-4768, 1996.
S. Maschauer et. al.: "A Series of 2-O-Trifluoromethylsulfonyl-D-Mannopyranosides as Precursors for Concomitant 18F-Labeling and Glycosylation by Click Chemistry," Carbohydrate Research, vol. 344, pp. 753-761, 2009.
S. Maschauer et. al.: "Labeling and Glycosylation of Peptides Using Click Chemistry: A General Approach to 18F-Glycopeptides as Effective Imaging Probes for Positron Emission Tomography," Angewandte Chemie, vol. 49, pp. 976-979, 2010.
D. O'Hagan et. al.: "Biosynthesis of an Organofluorine Molecule: A Fluorinase Enzyme has Been Discovered that Catalyzes Carbon-Fluorine Bond Formation," Nature, vol. 416, p. 279, Mar. 21, 2002.
D. E. Olberg et. al.: "Labeling Strategies of Peptides with 18F for Positron Emission Tomography," Current Topics in Medicinal Chemistry, vol. 10, pp. 1669-1679, 2010.
A. Orlova et. al.: "Tumor Imaging Using a Picomolar Affinity HER2 Binding Affibody Molecule," Cancer Research, vol. 66, pp. 4339-4348, 2006.
C. Phenix et. al.: "Imaging of Enzyme Replacement Therapy Using PET," PNAS, vol. 107, No. 24, pp. 10842-10847, Jun. 15, 2010.
T Poethko et. al.: "Chemoselective Pre-Conjugate Radiohalogenation of Unprotected Mono- and Multimeric Peptides Via Oxime Formation," Radiochim. Acta, vol. 92, pp. 317-327, 2004.
T. Poethko et. al.: "Two-Step Methodology for High-Yield Routine Radiohalogenation of Peptides: 18F-Labeled RGD and Octreotide Analogs," The Journal of Nuclear Medicine, vol. 45, pp. 892-902, 2004.
O. Prante et. al.: "3,4,6-Tri-O-Acetyl-2-Deoxy-2-[18F]Fluoroglucopyranosyl Phenylthiosulfonate: A Thiol-Reactive Agent for the Chemoselevtive 18F-Glycosylation of Peptides," Bioconjugate Chemistry, vol. 18, pp. 254-262, 2007.
M. Schottelius et. al.: "First 18F-Labeled Tracer Suitable for Routine Clinical Imaging of SST Receptor-Expressing Tumors Using Positron Emission Tomography," Clinical Cancer Research, vol. 10, pp. 3593-3606, 2004.
M. Schottelius et. al.: "Modulation of Pharmacokinetics of Radioiodinated Sugar-Conjugated Somatostatin Analogues by Variation of Peptide Net Charge and Carbohydration Chemistry," Bioconjugate Chemistry, vol. 16, pp. 429-437, 2005.
A. Shields: "PET Imaging with 18F-FLT and Thymidine Analogs: Promise and Pitfalls," The Journal of Nuclear Medicine, vol. 44, No. 9, pp. 1432-1434, Sep. 2003.
M. Ebner et. al.: "Glucose Isomerase Catalysed Isomerisation Reactions of 2R.3R)-Configured Aldofuranoses into the Corresponding Open-Chain 2-Ketoses," Carbohydrate Research, vol. 305, pp. 331-336, 1998.
H. Kissman et. al.: "5-Deoxy-5-Fluoro-D-Ribofuranosyl Derivatives of Certain Purines, Pyrimidines and 5,6-Dimethylbenzimidazole," Journal American Chemical Society, vol. 80, pp. 5559-5564, Oct. 20, 1958.

* cited by examiner

METHOD OF LABELLING A BIOLOGICALLY ACTIVE MOLECULE WITH 5-FLUORO-5-DEOXYPENTOSE OR A 3-FLUORO-3-DEOXYPENTOSE

BACKGROUND

The present invention relates to conjugates of biologically active compounds, such as proteins or peptides, and fluorine-labelled sugars, in particular 5-fluoro-5-deoxy or 3-fluoro-3-deoxy pentoses, processes for making these and the use of such conjugates, particularly those comprising 5-$^{18}$F-5-deoxypentoses or 3-$^{18}$F-3-deoxypentoses, in imaging, in particular positron emission tomography imaging.

INTRODUCTION

The fluorine-18 isotope is used very widely for medical imaging applications by positron emission tomography (PET). It has a half-life of 110 minutes and thus methods for preparing and manipulating $^{18}$F-containing molecules need to be rapid. The most commonly used carbohydrate for PET is 2-$^{18}$fluoro-2-deoxy-glucose (2-[$^{18}$F]-FDG, commonly referred to as FDG, i.e. so that the context implies $^{18}$F-labelling), which accounts for more that 90% of all fluorine-18 labelling studies in the clinic internationally. FDG is most commonly administered to cancer patients for tumor detection and monitoring, and for this reason 2-FDG is prepared rapidly from fluoride-18 (produced on a cyclotron) in many PET centres and hospitals worldwide.

There is a growing demand for labelling, or ligating, biologically active entities, such as peptides and proteins, with $^{18}$F. Peptides and proteins can be designed specifically to recognise disease tissue or disease cell types and, if labelled with fluorine-18 and injected into a patient, an image of diseased tissue/cell types can be generated. $^{18}$F-containing protein conjugates can thus be used for imaging (for example by PET), thereby allowing clinicians to diagnose or monitor disease.

A significant technological challenge lies in achieving efficient attachment of the fluorine-18 isotope to the protein. Small hydrophobic $^{18}$F-containing molecules, including fluoroaromatics such as 4-[$^{18}$F] fluorobenzaldehyde have been used in this regard. However, it is desirable to append water-soluble tags so that the overall properties of the resultant $^{18}$F-labelled protein do not deviate too significantly from those of the parent protein.

Small carbohydrates offer the opportunity to address the problem found with the use of fluoroaromatic compounds and in this context FDG has been widely explored as the labelling molecule (see, for example, WO 2005/086612 A2 (Immunomedics, Inc.), because it is readily available, owing to its existing clinical usage. The ligation of FDG to proteins remains a chemical challenge with few efficient conjugation methods having been developed. Oxime formation, however, is among the most amendable methods for achieving sugar ligation (see R. Haubner, H. J. Wester, F. Burkhart, R. Senekowitsch-Schmidtke, W. Weber, S. L. Goodman, H. Kessler and M. Schwaiger, *J. Nucl. Med.* 2001, 42, 326-336; M. Schottelius, F. Rau, J. C. Reubi, M. Schwaiger and H.-J. Wester, *Bioconjugate Chem.* 2005, 16, 429-437; R. D. Egleton and T. P. Davis, *NeuroRx,* 2005, 2, 44-53; and D. E. Olberg and O. K. Hjelstuen, *Curr. Topics Med. Chem.,* 2010, 10, 1669-1679).

To date, FDG is in fact the only fluorinated sugar that has been used to form oximes with peptides. Conveniently, FDG is prepared at, or delivered to, virtually all PET centres worldwide. However, a major problem with protein-FOG ligations is poor efficiency in forming the desired conjugates, e.g. via oxime formation. Consequentially, high reaction temperatures (up to 130° C.) and very low pHs (as low as 1-2) have to be used to allow adequate efficiency of the conjugation reactions. However, such conditions are undesirable: high temperature and low pH are unsuitable for most proteins and peptides, which are susceptible to degradation under such conditions.

Two recent publications (in 2010) have described the development of alternative, more elaborate, methods to address the problem of poor ligation efficiency of FDG to proteins.

The first involved a mechanism-based inhibition of the enzyme glucocerebrosidase (GCase) by [$^{18}$F]-FDG which secured a [$^{18}$F]-FDG molecule at the active site (C. P. Phenix, B. P. Rempel, K. Colobong, D. J. Doudet, M. J. Adam, L. A. Clarke and S. G. Withers. *PNAS,* 2010, 107, 10842-10847). However, this method is restricted to the GCase enzyme, and related enzymes, and is thus not generally applicable.

The second method described involves the initial incorporation of an azide at the 1-position of the FDG so as to allow a so-called 'Click' reaction with an acetylene-containing amino acid engineered into the protein (see O. Boutureira, F. D'Hooge, M. Fernandez-Gonzalez, G. J. L. Bernardes, M. Sanchez-Navarro, J. R. Koeppe and B. G. Davis, *Chem. Commun.,* 2010, 46, 8142-8144; S. Maschauer and O. Prante, *Carbohydr. Res.* 2009, 344, 753-761; S. Maschauer, J. Einsiedel, R. Haubner, C. Hocke, M. Ocker, H. Hubner, T. Kuwert, P. Gmeiner and O. Prante, *Angew. Chem. Int. Ed.* 2010, 49, 976-979; and O. Prante, J. Einsiedel, R. Haubner, P. Gmeiner, H.-J. Wester, T. Kuwert and S. Maschauer, *Bioconjugate Chem.* 2007, 18, 254-262). The need for modification of FDG so as to allow introduction of the azide functionality reduces the efficiency of the overall conjugation process, which is undesirable.

It is therefore desirable to provide an alternative way of making $^{18}$F-labelled biologically active molecules, such as proteins and peptides, so as to address one or more of the deficiencies in the art described or alluded to above.

SUMMARY

Having studied the poor efficiency in the oxime-forming reactions between FDG and proteins, we postulated that this may arise from the tendency of FDG to exist in a ring-closed pyranose form rather than as a ring-open aldehyde-containing compound. Whilst this is a phenomenon well-known for aldohexoses, we reasoned that, with FDG, the location of the electronegative fluorine atom at the 2-position will suppress ring opening to the aldehyde and drive the equilibrium still further towards the pyranose form, thereby suppressing the rate of conjugation with an aminooxy-containing molecule. Where it is desired to react the aldehyde functionality with an aminooxy functionality to provide an oxime, we reasoned that this tendency could explain the poor ligation efficiencies in the prior art.

We further reasoned that, in addition to the specific positioning of the fluorine, a 5-membered ring opens more quickly than a 6-membered ring.

In consequence of these considerations, but not being bound by them, we have found that 5-fluoro-5-deoxy or 3-fluoro-3-deoxy pentoses, for example 5-$^{18}$fluoro-5-deoxy or 3-$^{18}$fluoro-3-deoxy pentoses, participate more efficiently in ligation reactions, particularly ligation reactions involving amination of the carbonyl group in the open-chain form of such deoxypentoses, than fluorinated carbohydrate molecules generally, and FDG in particular.

Viewed from a first aspect, therefore, the invention provides a conjugate comprising a biologically active molecule and a 5-fluoro-5-deoxypentose or a 3-fluoro-3-deoxypentose.

Viewed from a second aspect, the invention provides a method of making a conjugate according to the first aspect of the invention comprising reacting a biologically active molecule with a 5-fluoro-5-deoxypentose or a 3-fluoro-3-deoxypentose.

Viewed from a third aspect, the invention provides a composition comprising a conjugate of the first aspect of the invention together with a pharmaceutically acceptable carrier or diluent.

Viewed from an fourth aspect, the invention provides a conjugate or composition of the invention for use in a diagnostic method practised on the human or animal body.

Viewed from a fifth aspect, the invention provides a method of imaging a subject, comprising administering an $^{18}$F-containing conjugate or composition of the invention to the subject and imaging the distribution of the $^{18}$F within the subject, typically using PET.

Viewed from a sixth aspect, the invention provides a method of diagnosis of a disease or condition, wherein an $^{18}$F-containing conjugate or composition of the invention is administered to a subject, the distribution of the $^{18}$F within the subject is imaged and the disease or condition, if present in the subject, is diagnosed.

According to further aspects of the invention related to the fifth and sixth aspect of the invention, administration of the conjugate or composition of the invention has been effected prior to the imaging according to the fifth and sixth aspects.

Viewed from a seventh aspect, the invention provides an $^{18}$F-containing conjugate or composition of the invention for use in a method of diagnosis of a disease or condition, wherein the conjugate or composition is administered to a subject, the distribution of the $^{18}$F within the subject is imaged and the disease or condition, if present in the subject, is diagnosed.

Viewed from a eighth aspect, the invention provides an $^{18}$F-containing conjugate or composition of the invention for use in a method of imaging a subject, comprising administering by parenteral administration, for example injection, a conjugate or composition of the invention to the subject and imaging the distribution of the $^{18}$F within the subject, typically using PET.

Viewed from ninth and tenth aspects of the invention is provided a conjugate of the invention for use in the manufacture of a medicament for use in a method according to the fifth or sixth aspect of the invention.

Other aspects and embodiments of the invention will be evident from the more detailed discussion of the invention, and examples thereafter, which follow below.

BRIEF DESCRIPTION OF THE FIGURES

FIG. 6 depicts a scheme for the conjugation of glutathione-derived aminooxy compound 3a with cold FDR (1b; 5-[$^{19}$F]-FDR) to provide a $^{19}$F-labelled oxime conjugate 4a.

DETAILED DESCRIPTION

Figure 1:
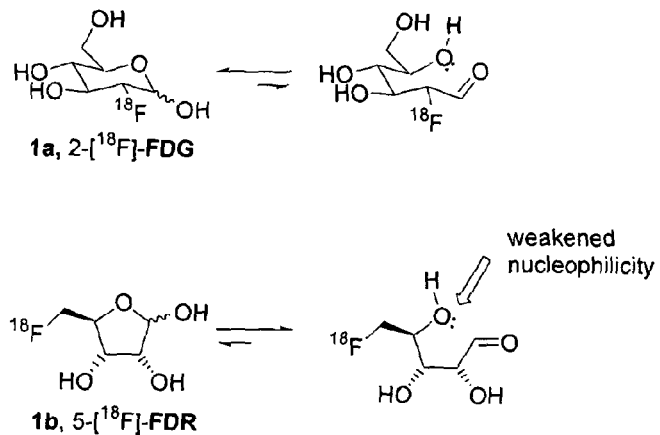
FIG. 1 depicts the equilibrium between the pyranose and open-chain forms of 2-[$^{18}$F]-FDG (1a) and 5-[$^{18}$F]-FDR (1b).

The present invention is based on our finding that 5-fluoro-5-deoxypentoses and 3-fluoro-3-deoxypentoses participate more efficiently in ligation reactions, particularly ligation reactions involving the amination of the carbonyl group of the deoxypentose in its open-chain form, for example so as to form oximes, than fluorinated carbohydrate molecules generally, and FDG in particular. This invention therefore usefully allows the provision of conjugates of deoxypentoses, labelled at the 5- and/or 3-positions with $^{18}$F, and biologically active molecules.

According to particular embodiments of all aspects of the present invention, the fluorine present at the 5- or 3-positions is $^{18}$F, and in particular, is present at the 5-position, whereby to provide 5-$^{18}$fluoro-5-deoxypentoses. The invention is described below with particular reference to these embodiments, but is not to be considered to be so limited.

The terms ligating or ligation used herein are intended to refer to the coupling of two or more molecules. As used herein, these terms are synonymous with the words conjugating and conjugation respectively. A conjugate is the product of a ligation, or conjugation, reaction.

As is known in the art, a pentose is a monosaccharide comprising five carbon atoms, and typically of the chemical formula C$_5$(H$_2$O)$_5$ (C$_5$H$_{10}$O$_5$). As is also known, pentoses may be either aldoses (aldopentoses) or ketoses (ketopentoses). The aldopentoses may be naturally derived (D-aldopentoses) or unnatural (L-aldopentoses). The natural aldopentoses are D-ribose, D-xylose, D-arabinose and D-lyxose. There are four corresponding unnatural L-aldopentoses. Of the ketopentoses, the 2-keto compounds (ribulose and xylulose) are more common.

Deoxy derivatives of pentoses, i.e. deoxypentoses, retain the essential five carbon atom-containing structure of the parent compound. By deoxypentoses is meant herein pentoses have one or more, typically one, two or three, of the hydroxyl groups in the parent compound independently replaced with a hydrogen atom or alternative substituent. Where the substituent at the "x" position in a x-deoxypentose is not specified, convention dictates that the hydroxyl group has been replaced with a hydrogen atom. Thus, a 2-deoxyribose is a derivative of ribose in which the 2-hydroxy group of ribose is replaced with an unspecified substituent, which may be hydrogen; and 2-deoxyribose is a derivative of ribose in which the 2-hydroxy group of ribose is replaced with hydrogen.

In the deoxypentoses present in the conjugates of the invention, at least the 5-hydroxyl group in the parent pentose is absent, and substituted with a fluorine atom, in some embodiments fluorine-18; and/or the 3-hydroxyl group in the parent pentose is absent, and substituted with a fluorine atom, in some embodiments fluorine-18. In other words, the conjugates of the first aspect of the invention comprise a 5-fluoro-5-deoxypentose, a 3-fluoro-3-deoxypentose or a 3,5-difluoro-3,5-dideoxypentose, it to be understood hearing that a 3,5-difluoro-3,5-dideoxypentose is an example of both a 5-fluoro-5-deoxypentose and a 3-fluoro-3-deoxypentose.

In some embodiments, the deoxypentoses that are labelled at the 3- and/or 5-positions with fluorine are 2-deoxypentoses, for example are 5-fluoro-2,5-dideoxy, 3-fluoro-2,3-dideoxy, 5-fluoro-2,3,5-trideoxy or 3-fluoro-2,3,5-trideoxy pentoses, for example 3,5-difluoro-2,3,5-trideoxy pentoses.

The absent hydroxyl group in a deoxypentose, when it is not replaced with a fluorine atom, may be replaced with a substituent selected from the group consisting of hydrogen, halo other than fluoro, alkyl, alkenyl, alkynyl, amino ($-NH_2$), dialkylamino, and alkoxy). Typically, the absent hydroxyl group of a 2-deoxypentose is not replaced with a halogen, in particular is not replaced with a fluorine atom.

Examples of deoxypentoses present in conjugates of the invention thus include 2-, 3- and 5-deoxypentoses, for example 5-fluoro-2,5-dideoxyriboses such as 5-fluoro-2,5-dideoxyribose, 3-fluoro-2,3-dideoxyriboses such as 3-fluoro-2,3-dideoxyribose, 5-fluoro-3,5-dideoxyriboses such as 5-fluoro-3,5-dideoxyribose and 3-chloro-5-fluoro-3,5-dideoxyribose, 5-fluoro-2,3,5-trideoxyriboses such as 5-fluoro-2,3,5-trideoxyribose, 3-fluoro-2,3,5-trideoxyriboses such as 3-fluoro-2,3,5-trideoxyribose and 3,5-difluoro-2,3,5-trideoxyriboses such as 3,5-difluoro-2,3,5-trideoxyribose, including alkyl, amino and alkoxy derivatives of any of the foregoing in which a carbon atom of a deoxyribose missing a hydroxyl group not specified as having an alternative substituent is substituted with an alkyl, amino or alkoxy substituent.

By alkyl is meant herein a saturated hydrocarbyl radical, which may be straight-chain, cyclic or branched (typically straight-chain). Where hydrocarbyl group has one or more sites of unsaturation, these may be constituted by carbon-carbon double bonds or carbon-carbon triple bonds. Where an alkyl group comprises a carbon-carbon double bond this provides an alkenyl group; the presence of a carbon-carbon triple bond provides an alkynyl group. Typically alkyl, alkenyl and alkynyl groups will comprise from 1 to 10 carbon atoms, more usually 1 to 6 carbon atoms it being understood that the lower limit in alkenyl and alkynyl groups is 2 carbon atoms and in cycloalkyl groups 3 carbon atoms.

Halo is fluoro, bromo, chloro or iodo.

Alkyloxy (synonymous with alkoxy) is of the formulae —O-alkyl, where alkyl is as defined hereinbefore.

A dialkylamino group is of the formula $-N(R)_2$ in which each R is independently alkyl or in which the two Rs attached to the nitrogen atom N are connected to form an alkylene diradical (derived formally from an alkane from which two hydrogen atoms have been abstracted, typically from terminal carbon atoms) whereby to form a ring together with the nitrogen atom N.

Typically, the 5-fluoro-5-deoxypentoses or 3-fluoro-3-deoxypentoses, e.g. 5-$^{18}$fluoro-5-deoxypentoses or 3-$^{18}$fluoro-3-deoxypentoses, according to the various aspects of the invention are aldodeoxypentoses, in particular aldodeoxy-D-pentoses. According to particular embodiments of the various aspects of the invention the deoxypentose labelled at the 5- or 3-position with $^{18}$F is a D-deoxyribose. Thus, according to particular embodiments of the various aspects of the present invention the deoxypentose is a 5-deoxy-5-$^{18}$fluoro-aldopentose, e.g. a 5-deoxy-5-$^{18}$fluoro-D-aldopentose. According to particular embodiments of the invention the deoxypentose labelled at the 5- or 3-position with $^{18}$F is a 5-deoxy-5-$^{18}$fluororibose or 3-deoxy-3-$^{18}$fluororibose, in particular 5-deoxy-5-$^{18}$fluoro-D-ribose or 3-deoxy-3-$^{18}$fluoro-D-ribose. 5-Deoxy-5-$^{18}$fluoro-D-ribose is referred to hereinafter as FDR or hot FDR (cold FOR refers herein to 5-deoxy-5-$^{19}$-fluoro-D-ribose) and discussion of the invention focuses on this particular embodiment. However, the invention is not to be understood to be so limited. In the discussion herein, compound 1b can be either (hot) FDR or cold FDR as the context dictates.

Figure 9:
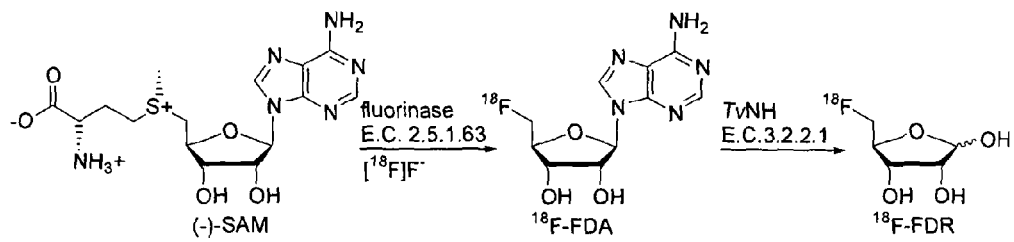
FIG. 9 depicts a known enzymatic synthesis of $^{18}$F-fluororibose (1b; $^{18}$F-FDR).

5-Fluoro-5-deoxypentoses and 3-fluoro-3-deoxypentoses, e.g 5-$^{18}$fluoro-5-deoxypentoses or 3-$^{18}$fluoro-3-deoxypentoses, including but not limited to FDR, can be prepared by both chemical and enzymatic methods. FDR, for example, is well-described in the literature (see in particular M Onega et al., *Chem. Commun.*, 2010, 46, 139-141, in which an enzymatic route to its synthesis is described, and literature referred to therein; see also FIG. 9 herein). The skilled person will readily be able to synthesise other 5-fluoro-5-deoxypentoses and 3-fluoro-3-deoxypentoses.

Particular conjugates of the present invention comprise a 5-$^{18}$F-labelled-5-deoxypentose, for example FDR, and a biologically active molecule so as to allow targeting of the conjugate to specific disease tissue or disease cell types. By biologically active molecule is meant herein a molecule that exhibits a pharmacological effect in a subject of interest, such as in a human or animal body.

There is no particular limit to the nature of the biologically active molecules that may be conjugated to the 5-fluoro-5-deoxypentoses or 3-fluoro-3-deoxypentoses, e.g 5-$^{18}$fluoro-5-deoxypentoses or 3-$^{18}$fluoro-3-deoxypentoses, provided that the biologically active molecule is susceptible to conjugation to these deoxypentoses. As is discussed below, whilst the present invention is illustrated with a peptide and a protein, the skilled person will understand from the art that a wide variety of biologically active molecules, including but not limited to proteins, peptides (by which is meant a molecule comprising a sequence of between 2 and 300, for example from between 2 and 20, naturally occurring or non-naturally occurring amino acids), nucleic acids, oligosaccharides, polysaccharides and lipids, may be used in accordance with this invention. For example, the biologically active molecules may be a hormone, growth factor, antibody, for example chimeric, humanised or fully human antibody, or an antigen-binding fragment thereof. Typically, the biologically active molecule will have a molecular weight of less than 100,000 Da, generally less than 10,000 Da. According to these and other embodiments of the invention, the biologically active molecule may be a potential pharmaceutical.

In the examples below, the present invention is illustrated with the use of the peptide glutathione and an Affibody protein. Glutathione (a natural tripeptide) was chosen as a model peptide to optimise the conjugation conditions. To demonstrate the utility of the invention for potential medical application, the $^{19}$F-labelling of an Affibody is described.

This affibody is a short protein (6.9 kDa) engineered from the B-domain in the immunoglobulin-binding region of staphylococcal protein A (J. Löfblom, J. Feldwisch, V. Tolmachev, J. Carlsson, S. Ståhl and F. Y. Frejd, *FEBS Lett.* 2010, 584, 2670-2680). It has picomolar affinity to human epidermal growth factor receptor 2 (HER2) which is overexpressed in many types of cancer cells, e.g. breast cancer (A. Orlova, M. Magnusson, T. L. J. Eriksson, M. Nilsson, B. Larsson, I. Hoiden-Guthenberg, C. Widstrom, J. Carlsson, V. Tolmachev, S. Ståhl and F. Y. Nilsson, *Cancer Res.* 2006, 66, 4339-4348). So far, Affibody has been mainly attached with metal nuclides (e.g. $^{68}$Ga and $^{111}$In) for medical imaging (V. Tolmachev, M. Altai, M. Sandström, A. Perols, A. E. Karlström, F. Boschetti and A. Orlova, *Biocojugate Chem.* 2011, doi: dx.doi.org/10.1021/bc100470x). There were two publications concerning the synthesis of $^{18}$F-labelled Affibody (D. O. Kiesewetter, G. Kramer-Marek, Y. Ma and J. Capala, *J. Fluor. Chem.* 2008, 129, 799-805; and Z. Cheng, O. P, De Jesus, M. Namavari, A. De, J. Levi, J. M. Webster, R. Zhang, B. Lee, F. A. Syud and S. S. Gambhir, *J. Nucl. Med.* 2008, 49, 804-813), in both cases hydrophobic aromatic linkers were employed.

It will be understood that the nature of the target disease, tissue or cells that may be imaged is limited only by the availability of a suitable biologically active molecule for targeting a cell or tissue of interest. Any protein or peptide that binds to diseased tissue, such as cancer, for example by way of tumour-associated antigens, may thus be labeled with a 5-$^{18}$fluoro-5-deoxypentose or 3-$^{18}$fluoro-3-deoxypentose in accordance with this invention so as to allow imaging (e.g. so as to detect or monitor) the cell or tissue of interest. According to certain embodiments of the invention, therefore, the invention provides imaging of cancerous tissue whereby to allow diagnosis and monitoring of cancer.

Methods of conjugation of biologically active compounds to $^{18}$F-labelled molecules, including $^{18}$F-labelled aromatic compounds and FDG are well known in the art. As is known, the biologically active molecule may be conjugated to the compound of interest (here a 5-$^{18}$fluoro-5-deoxypentose or a 3-$^{18}$fluoro-3-deoxypentose) through a linking moiety, for example a water-soluble linking moiety. The term "linking moiety" or "linker" is a well-understood term in the art meaning a short (e.g. about 2 to 50, e.g. from about 3 to 10, atoms long) bifunctional moiety, serving, for example to derivatise a biologically active molecule so as to introduce desirable functionality allowing conjugation to the compound of interest. Other advantages are also generally conferred by the use of linkers. The art is replete with suitable linking moieties. For example, linking moieties may comprise one or more functionalities selected from the group consisting of aminooxy, ester, amine, disulfide and imide. For a review describing the use of linkers in antibody-drug conjugates see L. Ducry and B. Stump (*Bioconjugate Chem.*, 2010, 21(1), pp 5-13).

According to particular embodiments of the invention, derivatisation of the biologically active molecule serves to introduce a linking moiety displaying a nucleophilic amino functionality. This can participate in an amination of the carbonyl group present in the open-chain form of deoxypentoses. Such aminations include the reactions of hydrazide- or hydrazine-functionalised biologically active molecules with $^{18}$F-labelled deoxypentoses described herein, whereby to provide conjugates comprising hydrazone linkages; or the reaction of thiosemicabazide-functionalised biologically active molecules with the $^{18}$F-labelled deoxypentoses, whereby to provide conjugates comprising thiosemicarbazone linkages.

According to particular embodiments of the invention, derivatisation of the biologically active molecule may be effected to introduce a linking moiety displaying an aminooxy (—ONH$_2$) functionality. This derivatisation permits conjugation with a 5- or 3-fluoro-, e.g. $^{18}$F—, labelled deoxypentose or pentose through an oxime linkage. The conjugation methodology in this regard is well-known to those of skill in the art (see, for example, T Poethko et al. *J. Nucl. Med.*, 2004, 45, 892-902; T Poethko et al. Radiochim. Acta, 2004, 92, 317-327; and M. Schottelius at al., *Clin. Cancer Res,* 2004, 10, 3593-3606).

As has been mentioned above, it is a particular benefit of the invention that 5- or 3-fluoro-, e.g. $^{18}$F—, labelled deoxypentoses, in particular FDR, ligate particularly rapidly under reductive amination conditions, for example through the reaction of an aminooxy-functionalised biologically active material with a $^{18}$F-labelled deoxypentose, to form an oxime linkage. We demonstrate herein that such reactions proceed directly and efficiently and under mild conditions. In fact, the speed of the reaction is several orders of magnitude faster than that of 2-FDG. Conveniently, the conjugation reactions may be carried out in aqueous solution (optionally in the absence of organic solvent) at pHs of between 4 to 6, and at ambient temperature (for example between about 15° C. to about 40° C.), in relatively short time scales (for example durations of about 1 to 30 minutes, e.g. about 5 or about 7 to 30 min). It is of particular benefit that $^{18}$F-labelled deoxypentoses such as FDR can be conjugated to biologically active molecules, which may be optionally pre-activated, so as to introduce functionality suitable for reaction with the $^{18}$F-labelled deoxypentoses, which may be reacted without any need for prior derivatisation.

In the experimental section below, the invention is illustrated with the preparation of "cold" ($^{19}$F-containing) compounds. The skilled person will understand that the same chemistry will work when applied to the corresponding $^{18}$F-containing compounds, a reaction scheme for which is depicted schematically in FIG. 10.

Some of the $^{18}$F- and $^{19}$F-containing compounds described herein are novel per se and these constitute further aspects of the present invention. Thus, the invention also provides compounds having the following Structures:

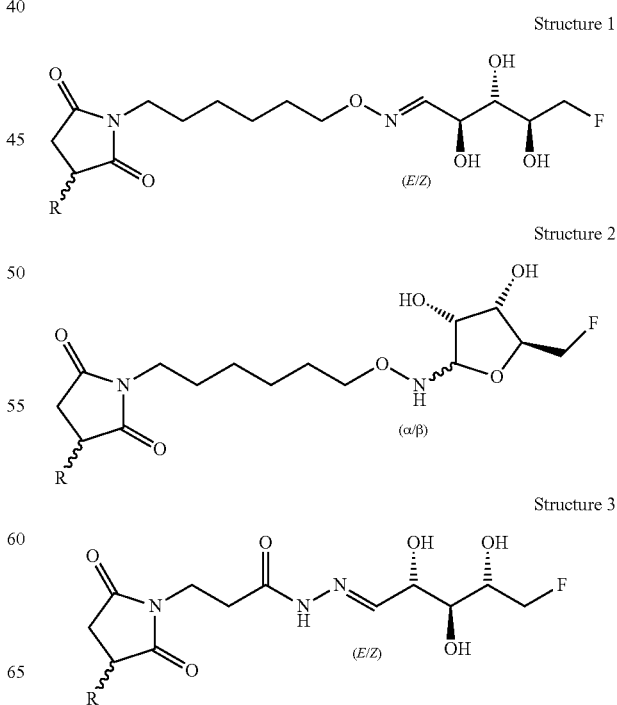

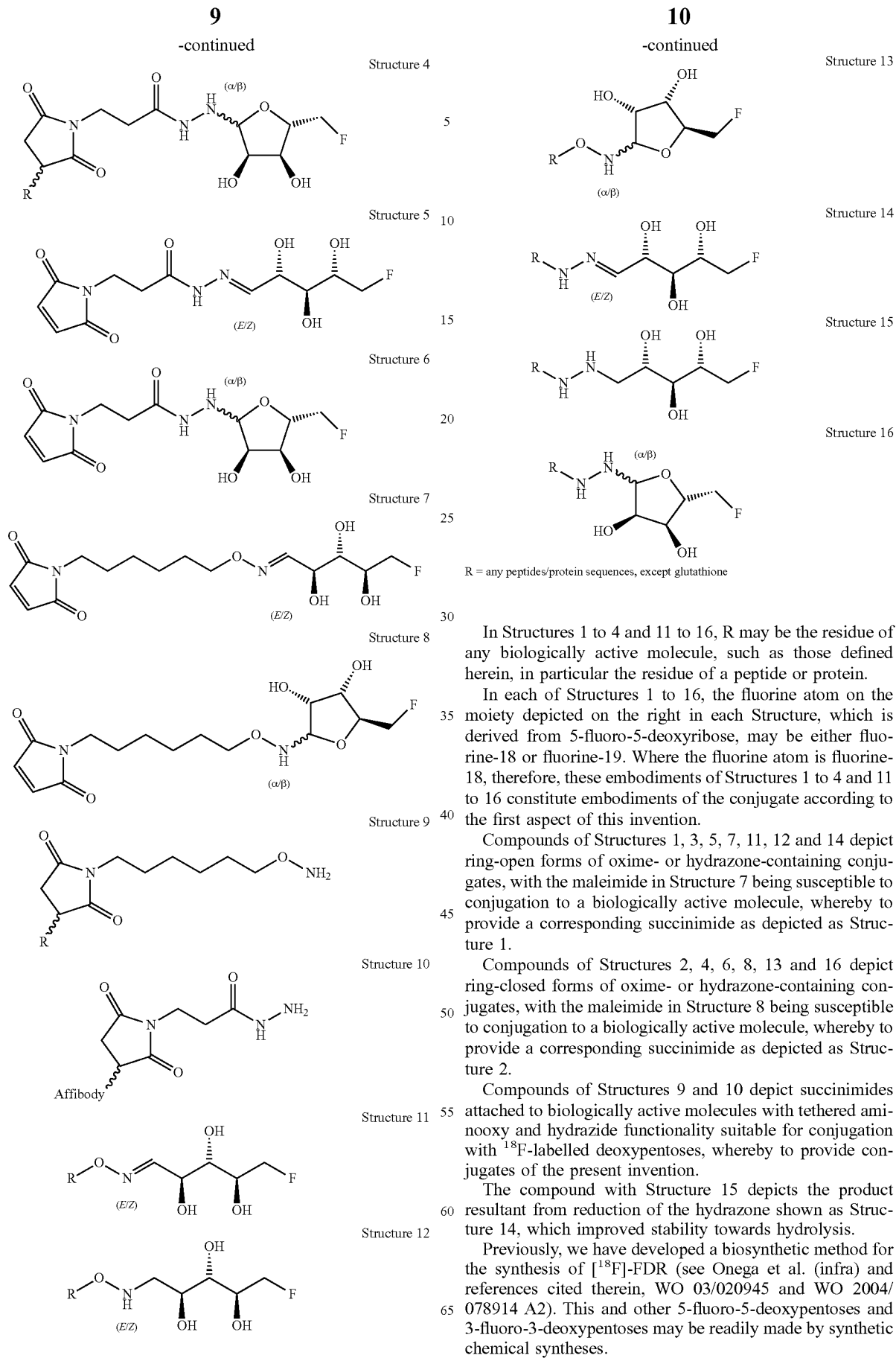

R = any peptides/protein sequences, except glutathione

In Structures 1 to 4 and 11 to 16, R may be the residue of any biologically active molecule, such as those defined herein, in particular the residue of a peptide or protein.

In each of Structures 1 to 16, the fluorine atom on the moiety depicted on the right in each Structure, which is derived from 5-fluoro-5-deoxyribose, may be either fluorine-18 or fluorine-19. Where the fluorine atom is fluorine-18, therefore, these embodiments of Structures 1 to 4 and 11 to 16 constitute embodiments of the conjugate according to the first aspect of this invention.

Compounds of Structures 1, 3, 5, 7, 11, 12 and 14 depict ring-open forms of oxime- or hydrazone-containing conjugates, with the maleimide in Structure 7 being susceptible to conjugation to a biologically active molecule, whereby to provide a corresponding succinimide as depicted as Structure 1.

Compounds of Structures 2, 4, 6, 8, 13 and 16 depict ring-closed forms of oxime- or hydrazone-containing conjugates, with the maleimide in Structure 8 being susceptible to conjugation to a biologically active molecule, whereby to provide a corresponding succinimide as depicted as Structure 2.

Compounds of Structures 9 and 10 depict succinimides attached to biologically active molecules with tethered aminooxy and hydrazide functionality suitable for conjugation with $^{18}$F-labelled deoxypentoses, whereby to provide conjugates of the present invention.

The compound with Structure 15 depicts the product resultant from reduction of the hydrazone shown as Structure 14, which improved stability towards hydrolysis.

Previously, we have developed a biosynthetic method for the synthesis of [$^{18}$F]-FDR (see Onega et al. (infra) and references cited therein, WO 03/020945 and WO 2004/078914 A2). This and other 5-fluoro-5-deoxypentoses and 3-fluoro-3-deoxypentoses may be readily made by synthetic chemical syntheses.

This invention offers significant advantages for protein labelling and could find general use in PET centers across the world both for research and for clinical purposes. The experimental section below illustrates both the significantly greater reactivity of FDR in a illustrative conjugation reaction in comparison with other sugars and that a typical conjugation is technically very straightforward, using existing conjugation methodologies with which the skilled person is very familiar.

It will be appreciated that the conjugates of the present invention and other compounds described herein may exist in various stereoisomeric forms. These compounds are to be understood to include all stereoisomeric forms and mixtures thereof, including enantiomers, diastereomers and racemic mixtures. The present invention includes within its scope the use of any such stereoisomeric form or mixture of stereoisomers, including the individual enantiomers and diastereomers of the conjugates of the invention as well as mixtures of such stereoisomers.

The skilled person will also understand that some conjugates of the invention will contain one or more basic functional groups, such as (alkyl)amino groups. Such conjugates are therefore capable of forming pharmaceutically acceptable salts with pharmaceutically acceptable acids. The term pharmaceutically acceptable salts is readily understood by those of normal skill, and is to be understood herein, to refer to relatively non-toxic, inorganic and organic acid addition salts of conjugates of the present invention. These salts may be prepared in situ in the administration vehicle, or by separately reacting a purified compound of the invention in its free base form with a suitable organic or inorganic acid, and isolating the salt thus formed during subsequent purification. Representative salts include inorganic salts such as hydrobromide, hydrochloride, sulfate, bisulfate, phosphate and nitrate salts; and organic acid salts such as tosylate, citrate, maleate, fumarate, succinate tartarate and acetate.

The skilled person will also understand that some conjugates of the invention will contain one or more acidic functional groups. Such conjugates are therefore capable of forming pharmaceutically acceptable salts with pharmaceutically acceptable bases. The term pharmaceutically acceptable salt in this context therefore refers to relatively non-toxic, inorganic and organic base addition salts of conjugates of the present invention. These salts can also be prepared in situ in the administration vehicle, or by separately reacting the purified compound in its free acid form with a suitable base, such as the hydroxide, carbonate or bicarbonate of a pharmaceutically acceptable metal cation such as lithium, sodium, potassium, calcium and magnesium, with ammonia, or with a pharmaceutically acceptable amine, such as ethylamine, diethylamine, ethylenediamine, ethanolamine, diethanolamine, piperidine and piperazine.

As noted above, the conjugates of the present invention are of utility in methods of imaging and diagnosis of the subject. In some embodiments of these aspects of invention, the subject will have been previously administered with a conjugate of the invention. In certain embodiments, the imaging is PET imaging and it is envisaged that the invention is readily susceptible to automation in PET centres.

In a typical PET investigation, a small amount of compound is administered to the subject, typically a human or other animal. Circulation within the subject allows the absorption of the compound, typically in targeted tissue/cell types. According to the present invention, the conjugates are intended to be preferentially retained in particular tissue types in the light of the biologically active molecule with which the $^{18}$F-labelled deoxypentose is conjugated. The distribution of the conjugate may then be imaged using PET. The resultant data constitutes useful quantitative spatial information to the clinician, which the clinician can use to reach a diagnosis. For example, differential accumulation of the conjugate may be indicative of a disease or cell type to which the conjugate has been targeted.

Amongst other benefits, PET allows investigations into in vivo biochemical changes or metabolic effects of a potential drug candidate. In this way PET can be used to measure drug distribution, thus allowing the evaluation of the pharmacokinetics and pharmacodynamics of a particular drug candidate under study. As is known in the art, PET be can used to quantify the presence of binding sites in tissues.

Typically the conjugates of the present invention are deployed as compositions comprising a conjugate of the present invention together with one or more pharmaceutically-acceptable carriers suitable for use in PET imaging, in an amount sufficient to yield a meaningful image using PET imaging equipment.

Suitable pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Typically, the conjugates will be administered parenterally, typically by injection. Introduction of the conjugates and the subject may be by one or more administration, e.g. injection. For such administration the conjugates will generally be formulated as a sterile, pyrogen-free, parenterally-acceptable aqueous solution according to the usual ability of those of normal skill in the art. A skilled clinician will determine any appropriate amount for a subject in question based on a subject's age, weight and sex as well as instrumental considerations.

Each document referred to herein (both patent and non-patent literature) is incorporated herein by reference as if the entire contents of each was recited in its entirety.

The invention is further illustrated by the non-limiting examples described below.

Preparation of $^{19}$F-Containing Conjugates (Cold Conjugates)

Figure 2:
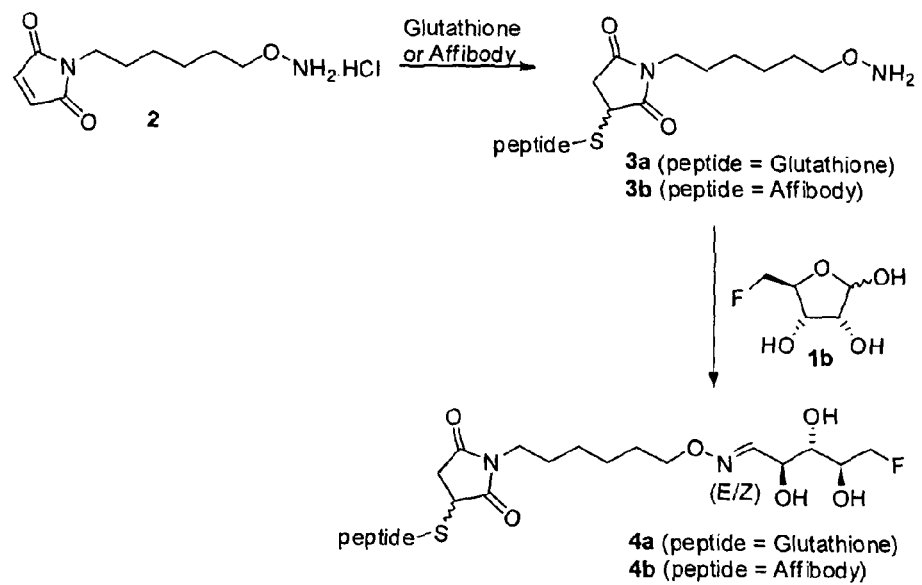
FIG. 2 depicts a scheme for conjugation of 5-[$^{19}$F]-FDR (1b) with peptides.

Experiments were carried out by using the endogenous tripeptide, glutathione, as a model peptide for the conjugation. FIG. 2 shows the synthetic scheme carried out, comprising conjugation between known linker 2 and glutathione or an Affibody protein to provide compounds 3a and 3b, which are then conjugated to $^{19}$F-containing FDR ($^{19}$F-containing compound 1b; cold FDR) to provide conjugates 4a and 4b.

Figure 3:
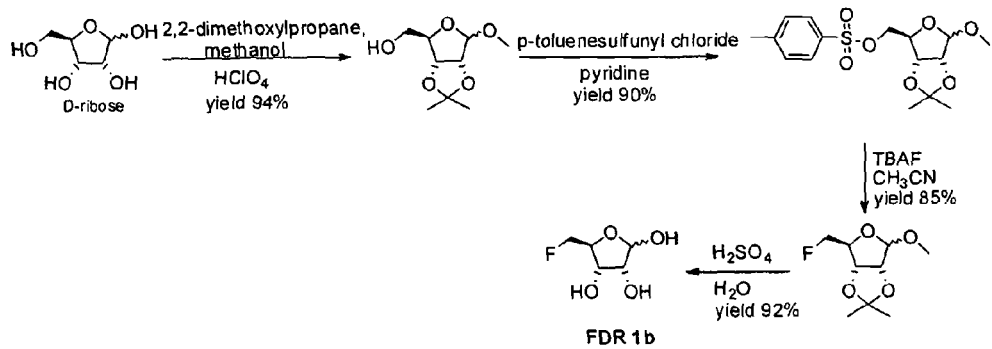
FIG. 3 depicts a known synthesis of cold FDR (1b; 5-[$^{19}$F]-FDR).
Figure 4:
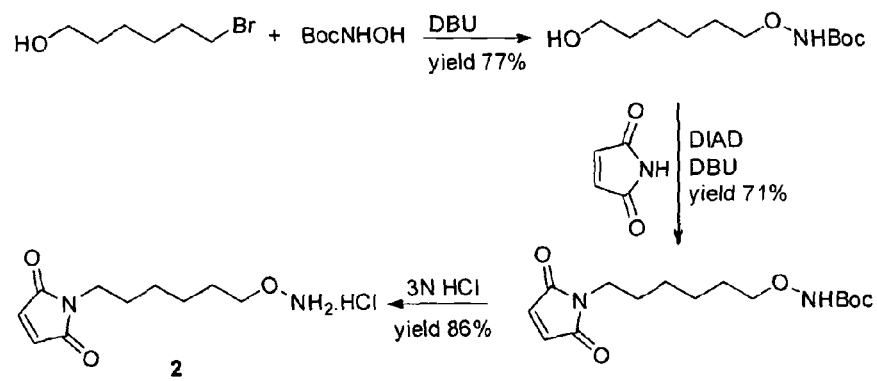
FIG. 4 depicts a known synthesis of an aminooxy compound 2.

The synthesis of cold FDR (1b; depicted in FIG. 3) was carried out according to published procedure (see T. Caren et at *Angew. Chem. Int. Ed.,* 2007, 46, 2325-2327; F. J. Lopez-Herrera at al. *Tetrahedron,* 1996, 52, 4757-4768; A. E. Stutz et al. *Carbohydr. Res.,* 1998, 305, 331-336; and M. J. Weiss et al. *J. Am. Chem. Soc.,* 1958. 80, 5559-5564).

Linker 2 was synthesized according to a published procedure (M. Berndt et al. *Nuclear Medicine Biology*, 2007, 34, 5-15).

Figure 5:
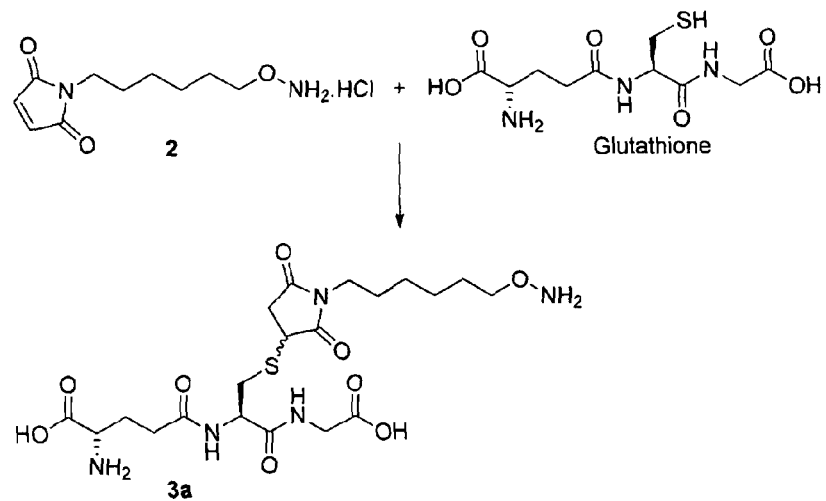
FIG. 5 depicts a typical synthesis of glutathione-derived aminooxy compound 3.

The conjugation between 2 and glutathione was accomplished in water at room temperature over 3 minutes, affording compound 3a with full conversion. A preparation of compound 3a is shown in FIG. 5. A typical example of a preparation carried out is as follows: a solution of linker 2 (12.4 mg, 50.0 μmol) and glutathione (15.4 mg, 50.0 μmol) in sterile water (1 mL) in an Eppendorf tube was incubated for 3 minutes at 25° C. HPLC analysis indicated that full conversion was achieved. The resultant solution of 3a (50 mM) in water was divided into aliquots and stored at −80° C. for further use. The thus-obtained 3a was used for subsequent conjugation without any need for purification. For analytical purposes, 3a was purified conveniently by passing through a C18 RP column.

Since the thiol group of glutathione attacks the carbon-carbon double bond of 2 from both sides, 3a was obtained as a mixture of diastereomers (as indicated), which explains the appearance of a shoulder in the HPLC trace of the purified compound.

Figure 6:
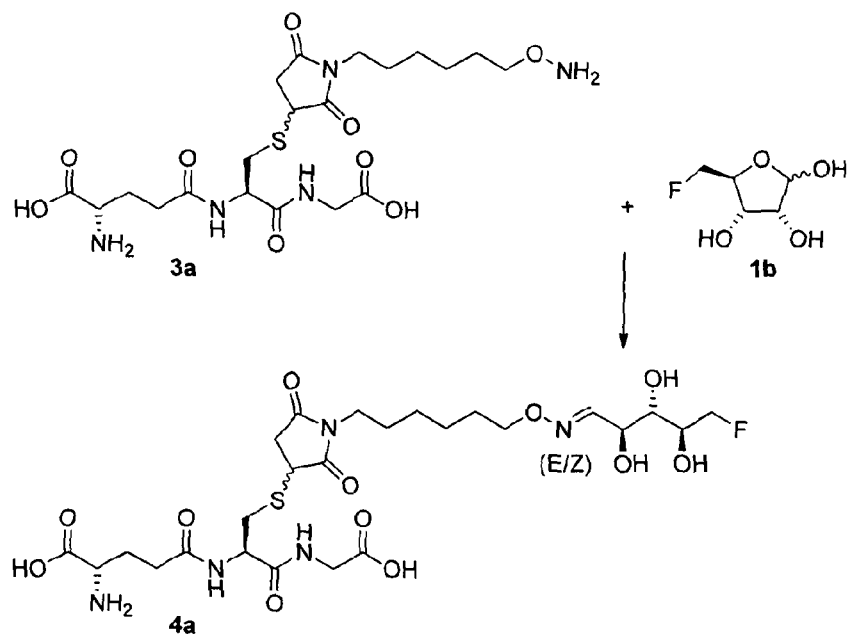

Literature (e.g. J. W. Haas, Jr. and R. E. Kadunce, *J. Am. Chem. Soc.*, 1962, 84, 4910-4913) indicated that optimum pH for D-ribose to form an oxime was around 4.6 at 25° C. Accordingly, compound 3a (20 mM) was incubated with FOR (1b) (20 mM) in sodium acetate buffer (0.25 M, pH 4.6) at 25° C., resulting in the formation of peptide-sugar conjugate 4a with full conversion in 7 minutes. A typical procedure for the preparation of conjugate 4a is depicted in FIG. 6. The following preparations were carried out:

Test Scale Experiments:

A solution of 3a (1.0 mg, 2.0 μmol) and FOR (0.3 mg, 2.0 μmol) in sodium acetate buffer (100 μL, 0.25 M, pH 4.6) in an Eppendorf tube was incubated at 25° C. Samples (2 μL each) were taken at intervals of time and were diluted with water by 50 times for HPLC analysis. Full conversion was reached in 7 minutes of reaction.

Preparative Scale Experiments:

A solution of 3a (10.4 mg, 20.0 μmol) and FDR (3.0 mg, 20.0 μmol) in sodium acetate buffer (1 mL, 0.25 M, pH 4.6) in an Eppendorf tube was incubated for 7 minutes at 25° C. The reaction mixture was loaded to a C18 RP cartridge column. The column was washed with water (5×2 mL, 0.1% formic acid) and subsequently with elution buffer (30% $CH_3CN$, 0.1% formic acid in $H_2O$, typically 10 mL). The fractions containing product 4a was combined and the combined solution was freeze-dried, affording white solid product 4a (12.9 mg, 19.8 μmol, isolated yield 99%). $^1H$ NMR (500 MHz, $CD_3OD$) δ 7.40 (d, J=6.8 Hz, 0.8H, N=CH, E-isomer), 6.78 (d, J=6.0 Hz, 0.2H, N=CH, Z-isomer), 4.93 (dd, J=6.0 Hz, 3.0 Hz, 0.2H, N=CHCH, Z-isomer), 4.58 (m, 1H), 4.43 (d, J=3.7 Hz, 1H), 4.37 (dd, J=6.8 Hz, 4.1 Hz, 0.8H, N=CHCH, E-isomer), 3.98 (m, 3H), 3.83 (s, 2H), 3.76, (m, 2H), 3.63 (t, J=7.0 Hz, 2H), 3.39 (t, J=7.0 Hz, 2H, $NCH_2$), 3.21 (m, 2H), 2.99 (1H), 2.60 (dddd, 1H), 2.21 (m, 2H), 2.02 (q, 2H), 1.43 (m, 4H), 1.20 (m, 4H). $^{19}F$ NMR (470 MHz, $D_2O$) δ −234.70 (ddt, J=47.4 Hz, 24.4 Hz), −235.38 (ddt, J=47.5 Hz, 25.5 Hz).

Figure 7:
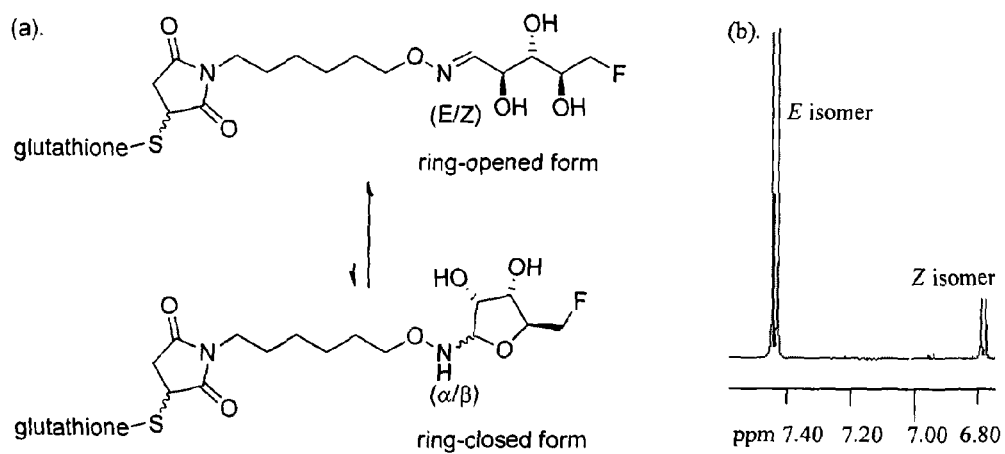
FIG. 7(a) shows the conformations of $^{19}$F-labelled conjugate 4a in D$_2$O at 20° C.
FIG. 7(b) depicts $^1$H NMR signals (N=CH) for the E- and Z-isomer of 4a, respectively.

To confirm the identity of the product, 4a was isolated by passing through an Alltech C18 cartridge/column and was analysed by mass spectroscopy (MS), 1D and 2D NMRs. As shown in FIG. 7, $^1H$ NMR indicates that the conjugate exists exclusively in ring-opened forms (E/Z ratio 4:1 at 20° C.) in solution ($D_2O$). The imine proton appears at 7.40 ppm (N=CH, d, J=6.8 Hz) for the E-isomer and the corresponding proton in the Z-isomer is at 6.78 (d, J=6.0 Hz). This simple conjugation may facilitate future GMP assessments for routine production of PET tracers. In contrast, the conjugation of 2-FDG to peptides/proteins generated several additional isomeric products (e.g. ring-closed, ring-opened). Thus the present invention allows the provision of a more homogenous product.

A stability study confirmed that the conjugate 4a is stable in phosphate-buffered saline (PBS) at least for 8 hours at 37° C., which is stable enough for PET applications.

Substrate concentration influences the conjugation efficiency of 4a and 1b. At pH 4.6, quantitative formation of 4a was observed in 3-7 minutes at 25° C., when a relatively high concentration of 3a (20-50 mM) was reacted with one equivalent of 1b (see Table 1, entry is 1 and 2). When a relatively low concentration of 3a (1 mM) and 1b (1 mM) was applied, it needed 110 minutes for the reaction to complete (entry 3) under otherwise identical conditions. The data shows, however, that conjugation between 3a and 1b may be achieved over a relatively wide pH range (2.6-6.0) of the reaction medium and within a reasonable reaction time (<30 minutes), the optimum pH being 4.6 (Table 1, entry 2). The feasibility of conjugation with FDR at pH 4-7 at 25° C. represents a clear advantage over the conjugation with FDG which requires pH values as low as pH 1-2 and temperature up to 130° C.

TABLE 1

Effect of substrate (3a and 1b) concentration and medium pH on conjugation efficiency at 25° C.

| Entry | 3a (mM) | 1b (mM) | pH (buffer, M) | Time for full conversion to product 4a (minutes) |
|---|---|---|---|---|
| 1 | 50 | 50 | 4.6 (sodium acetate, 0.25) | 3 |
| 2 | 20 | 20 | 2.6 (citric acid-$Na_2HPO_4$, 0.25) | 30 |
|  |  |  | 3.6 (citric acid-$Na_2HPO_4$, 0.25) | 15 |
|  |  |  | 4.6 (sodium acetate, 0.25) | 7 |
|  |  |  | 4.6 (sodium acetate, 0.50) | 7 |
|  |  |  | 6.0 (potassium phosphate, 0.25) | 30 |
|  |  |  | 7.0 (potassium phosphate, 0.25) | 100 |
| 3 | 1 | 1 | 4.6 (sodium acetate, 0.25) | 110 |

To confirm the hypothesis that fluorination at the 5-position of FDR 1b has a particular ability to enhance the rate of conjugation, conjugation with 3a was carried out with other sugars. Under the same reaction conditions 5-FDR 1b reacted significantly more quickly than the corresponding non-fluorinated D-ribose (Entry 1 and 2), and much more quickly than D-glucose (entry 3). The conjugation of 3a with 2-FDG (1b) was quite sluggish, the conversion being 48% over 18 hours of reaction, conditions which cannot be used for hot labelling experiments owing to this low efficiency.

TABLE 2

The conjugation between 3a (20 mM) and sugars (20 mM) at pH 4.6 at 25° C. (6-FDG = 6-fluoro-6-deoxy-D-glucose)

| Entry | Sugar | Reaction time (min) | Conversion (%) |
|---|---|---|---|
| 1 | FDR (1b) | 7 | >98 |
| 2 | D-ribose | 7 | 17 |
|  |  | 60 | 60 |
| 3 | D-glucose | 7 | 2 |
|  |  | 60 | 14 |

TABLE 2-continued

The conjugation between 3a (20 mM) and sugars (20 mM) at pH 4.6 at 25° C. (6-FDG = 6-fluoro-6-deoxy-D-glucose)

| Entry | Sugar | Reaction time (min) | Conversion (%) |
|---|---|---|---|
| 4 | 2-FDG (1a) | 7 | 1 |
|  |  | 60 | 7 |
|  |  | 1080 | 48 |
| 5 | 6-FDG | 60 | 25 |

In order to establish if the presence of a peptide sequence influences the conjugation product, protein-free conjugate 7 conjugate 7

Figure 8:
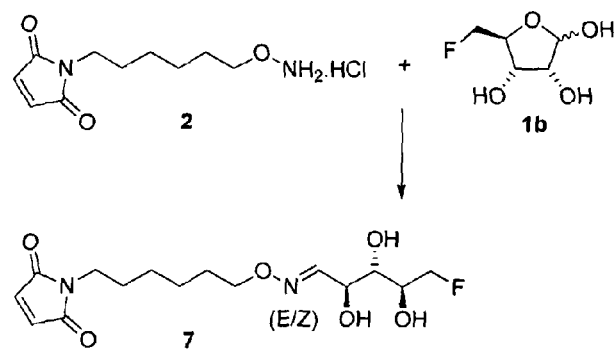
FIG. 8 depicts a scheme for the conjugation of aminooxy compound 2 with cold FDR (1b; 5-[$^{19}$F]-FDR) to provide a $^{19}$F-labelled oxime conjugate 7.

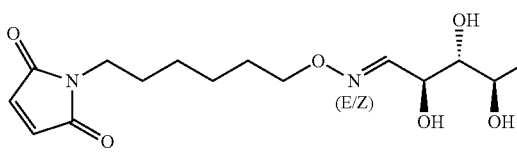

was prepared as depicted in FIG. 8. The following preparation was carried out:

A solution of linker 2 (12.4 mg, 50.0 µmol) and FDR 1b (7.6 mg, 50.0 µmol) in sodium acetate buffer (1 mL, pH=4.6, 0.25 M) in an Eppendorf tube was incubated for 7 minutes at 25° C. HPLC analysis indicated that full conversion was reached. The obtained reaction mixture was passed through a C18 RP column (Alltech, High Capacity C18). The column was washed with water (5 mL, containing 0.1% formic acid). Compound 7 was eluted from the column with a buffer (10% $CH_3CN$, 0.1% formic acid). The fractions containing 7 were combined and freeze-dried overnight, affording the product as a semisolid. $^1H$ NMR (400 MHz, $CDCl_3$) δ 7.44 (d, J=6.8 Hz, 0.8H, N=CH, E-isomer), 6.78 (d, J=6.0 Hz, 0.2H, N=CH, Z-isomer), 6.72 (s, 2H, maleimide), 4.93 (dd, J=6.0 Hz, 3.0 Hz, 0.2H, N=CHCH, Z-isomer), 4.58 (d, J=3.1 Hz, 1H), 4.46 (d, J=3.7 Hz, 1H), 4.36 (dd, J=6.8 Hz, 4.1 Hz, 0.8H, N=CHCH, E-isomer), 3.98 (t, J=6.6 Hz, 2H, $CH_2ON$), 3.76, (m, 1H), 3.73 (m, 1H), 3.39 (t, J=7.0 Hz, 2H, $NCH_2$), 1.55 (m, 4H), 1.20 (m, 4H). $^{18}F$ NMR (376 MHz, $D_2O$) δ −234.70 (dt, J=47.4 Hz, 24.4 Hz), −235.38 (dt, J=47.5 Hz, 25.5 Hz).

NMR analysis indicated an E- to Z-isomer ratio similar to 4a. This experiment therefore shows that the effective conjugation of aminooxy compound 3a with compound 1b was not attributable to the specific aminooxy-containing compound used.

Preparation of $^{18}F$-Containing Conjugates

Analogous methodology to that described above in connection with the synthesis of the cold 5-$^{19}$fluoro-containing conjugates may be used to prepare 3-$^{19}F$-containing and $^{18}F$-containing conjugates of the invention. For example, hot FDR can be routinely produced according to an enzymatic method ((see Onega et al. (infra) and references cited therein, WO 03/020945 and WO 2004/078914 A2), as depicted schematically in FIG. 9. Moreover, the skilled person is readily able to make other $^{18}F$-containing deoxypentoses by chemical synthesis.

Figure 10:
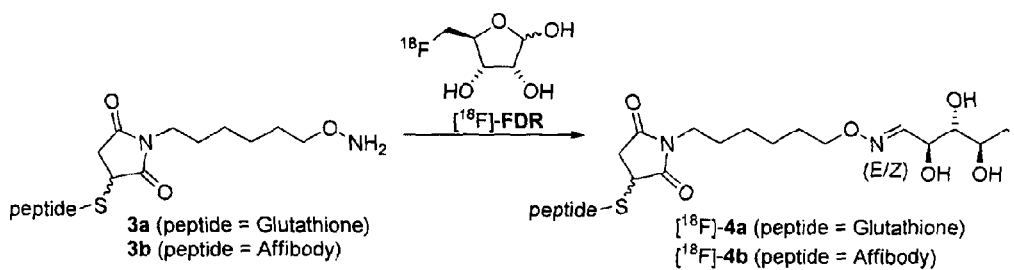
FIG. 10 depicts a scheme for conjugation of 5-[$^{18}$F]-FDR (1b) with peptides.

An example of the $^{18}F$-labelling of glutathione with an Affibody is depicted in FIG. 10. As the skilled person will appreciate, the chemistry involved is entirely analogous to that described above in connection with the preparation of the cold conjugates.

The invention may be further understood with regard to the following non-limiting clauses:

1. A conjugate comprising a biologically active molecule and a 5-fluoro-5-deoxypentose or a 3-fluoro-3-deoxypentose.

2. The conjugate of clause 1 wherein the 5-fluoro-5-deoxypentose or 3-fluoro-3-deoxypentose is an aldodeoxypentose.

3. The conjugate of clause 1 or clause 2 wherein the 5-fluoro-5-deoxypentose or 3-fluoro-3-deoxypentose is a 2-deoxypentose.

4. The conjugate of clause 3 wherein the 2-deoxypentose has a substituent at the 2-position selected from the group consisting of hydrogen, alkyl, alkenyl, alkynyl, amino, dialkylamino and alkoxy.

5. The conjugate of any one preceding clause wherein the 5-fluoro-5-deoxypentose or 3-fluoro-3-deoxypentose is a 5-fluoro-3,5-dideoxypentose or a 3-fluoro-3,5-dideoxypentose wherein the 5-fluoro-3,5-dideoxypentose has a substituent at the 3-position, and the 3-fluoro-3,5-dideoxypentose has a substituent at the 5-position, which substituents at the 3-position and 5-position are selected from the group consisting of hydrogen, halo, alkyl, alkenyl, alkynyl, amino, dialkylamino and alkoxy.

6. The conjugate of any one preceding clause wherein the 5-fluoro-5-deoxypentose or 3-fluoro-3-deoxypentose is a deoxy-D-ribose.

7. The conjugate of any one preceding clause wherein the biologically active molecule is conjugated to the deoxypentose via a linking moiety.

8. The conjugate of any one preceding clause wherein the biologically active molecule is conjugated to the deoxypentose by an oxime, hydrazone or thiosemicarbazone linkage.

9. The conjugate of clause 8, which has one of the following Structures:

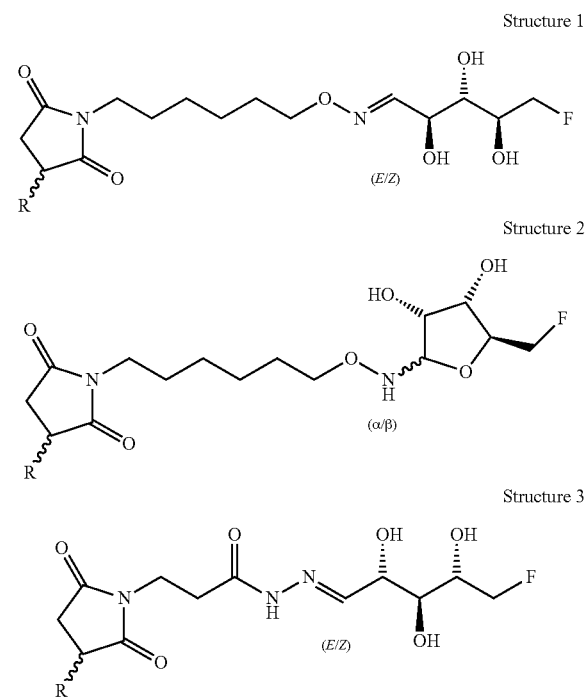

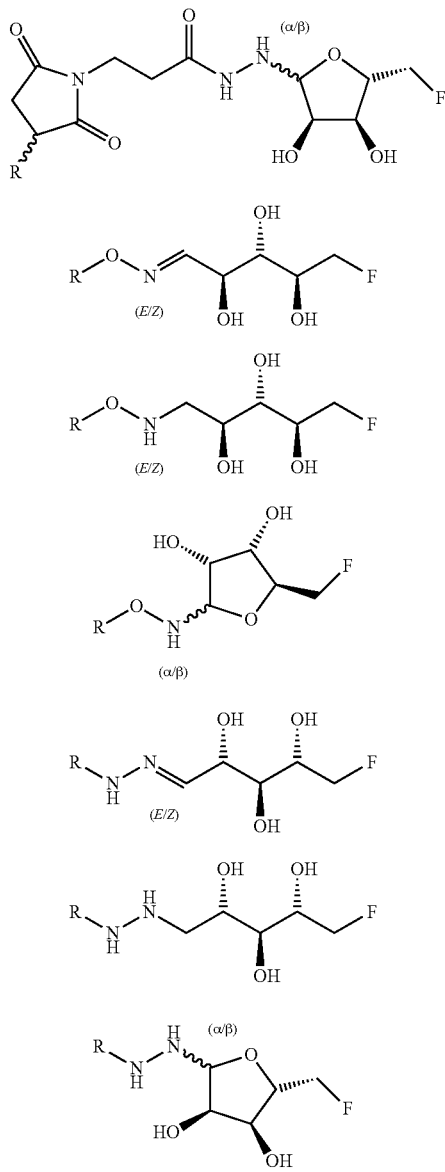

wherein R denotes the biologically active molecule.

10. The conjugate of clause 8 or clause 9 wherein the biologically active molecule is conjugated to the deoxypentose through an oxime linkage.

11. The conjugate of any one preceding clause wherein the biologically active molecule is a protein or peptide.

12. The conjugate of any one preceding clause wherein the 5-fluoro-5-deoxypentose or 3-fluoro-3-deoxypentose is a 5-$^{18}$fluoro-5-deoxypentose or a 3-$^{18}$fluoro-3-deoxypentose.

13. The conjugate of clause 12 wherein the 5-fluoro-5-deoxypentose or 3-fluoro-3-deoxypentose is a 5-deoxy-5-$^{18}$fluoro-D-ribose or a 3-deoxy-3-$^{18}$fluoro-D-ribose.

14. The conjugate of clause 13 wherein the 5-fluoro-5-deoxypentose or 3-fluoro-3-deoxypentose is 5-deoxy-5-$^{18}$fluoro-D-ribose or 3-deoxy-3-$^{18}$fluoro-D-ribose.

15. The conjugate of any one preceding clause wherein the 5-fluoro-5-deoxypentose or 3-fluoro-3-deoxypentose is a 5-fluoro-5-deoxypentose.

16. A method of making a conjugate as defined in any one of clauses 1 to 14 comprising reacting a biologically active molecule with a 5-fluoro-5-deoxypentose or a 3-fluoro-3-deoxypentose.

17. The method of clause 16 wherein the biologically active molecule is reacted with a 5-fluoro-5-deoxypentose.

18. The method of clause 16 or clause 17 wherein the biologically active molecule comprises an aminooxy functional group.

19. A composition comprising a conjugate as defined in any one of clauses 1 to 15 together with a pharmaceutically acceptable carrier or diluent.

20. The composition of clause 19 wherein the 5-fluoro-5-deoxypentose or 3-fluoro-3-deoxypentose in the conjugate is a $^{18}$F-deoxypentose.

21. A conjugate comprising a $^{18}$F-deoxypentose as defined in any one of clauses 1 to 15 for use in a diagnostic method practised on the human or animal body.

22. A method of imaging a subject, comprising administering a conjugate comprising a $^{18}$F-deoxypentose as defined in any one of clauses 1 to 15 or composition as defined in clause 20 to the subject and imaging the distribution of the $^{18}$F within the subject, typically using PET.

23. A method of diagnosis of a disease or condition, wherein a conjugate comprising a $^{18}$F-deoxypentose as defined in any one of clauses 1 to 15 or composition as defined in clause 20 is administered to a subject, the distribution of the $^{18}$F within the subject is imaged and the disease or condition, if present in the subject, is diagnosed.

24. A conjugate comprising a $^{18}$F-deoxypentose as defined in any one of clauses 1 to 15 or composition as defined in clause 20 for use in a method of diagnosis of a disease or condition, wherein the conjugate or composition is administered to a subject, the distribution of the $^{18}$F within the subject is imaged and the disease or condition, if present in the subject, is diagnosed.

25. A conjugate comprising a $^{18}$F-deoxypentose as defined in any one of clauses 1 to 15 or composition as defined in clause 20 for use in a method of imaging a subject, comprising administering by parenteral administration, for example injection, a conjugate or composition of the invention to the subject and imaging the distribution of the $^{18}$F within the subject, typically using PET.

26. A conjugate comprising a $^{18}$F-deoxypentose as defined in any one of clauses 1 to 15 for use in the manufacture of a medicament for use in a method as defined in clause 22 or clause 23.

The invention claimed is:

1. A conjugate of a biologically active molecule derivatized with a linking moiety comprising a nucleophilic amino moiety and a 5-[$^{18}$F]fluoro-5-deoxypentose or a 3-[$^{18}$F]fluoro-3-deoxypentose, wherein the biologically active molecule is selected from the group consisting of a protein, a peptide, a nucleic acid, an oligosaccharide, and a polysaccharide, wherein the biologically active molecule is conjugated to the deoxypentose by an oxime linkage.

2. A conjugate of claim 1 wherein the 5-[$^{18}$F]fluoro-5-deoxypentose or 3-[$^{18}$F]fluoro-3-deoxypentose is an aldodeoxypentose.

3. A conjugate of claim 1 wherein the 5-[$^{18}$F]fluoro-5-deoxypentose or 3-[$^{18}$F]fluoro-3-deoxypentose is a further 2-deoxypentose.

4. A conjugate of claim 3 wherein the 2-deoxypentose has a substituent at the 2-position selected from the group consisting of hydrogen, alkyl, alkenyl, alkynyl, amino, dialkylamino and alkoxy.

5. A conjugate of claim 1 wherein the 5-[$^{18}$F]fluoro-5-deoxypentose or 3-[$^{18}$F]fluoro-3-deoxypentose is a 5-fluoro-3,5-dideoxypentose or a 3-fluoro-3,5-dideoxypentose wherein the 5-fluoro-3,5-dideoxypentose has a substituent at the 3-position, and the 3-fluoro-3,5-dideoxypentose has a substituent at the 5-position, wherein the substituents at the 3-position and 5-position are selected from the group consisting of hydrogen, halo, alkyl, alkenyl, alkynyl, amino, dialkylamino and alkoxy.

6. A conjugate of claim 1 wherein the 5-[$^{18}$F]fluoro-5-deoxypentose or 3-[$^{18}$F]fluoro-3-deoxypentose is a deoxy-D-ribose.

7. A conjugate of claim 1, comprising one of the following Structures:

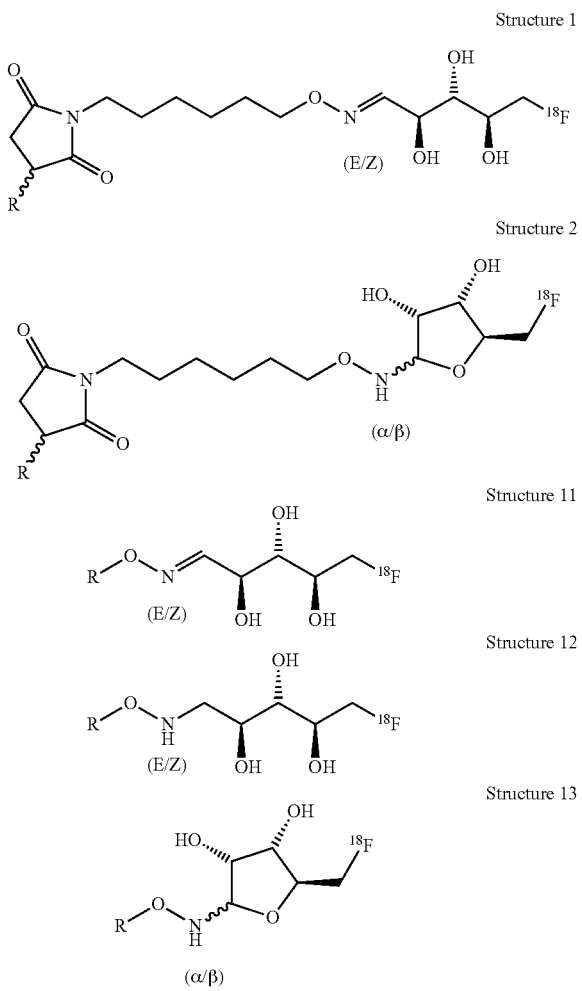

wherein R denotes the biologically active molecule.

8. A conjugate of claim 1 wherein the biologically active molecule is a protein or peptide.

9. A conjugate of claim 1 wherein the 5-[$^{18}$F]fluoro-5-deoxypentose or 3-[$^{18}$F]fluoro-3-deoxypentose is a 5-deoxy-5-[$^{18}$F]fluoro-D-ribose or a 3-deoxy-3-[$^{18}$F]fluoro-D-ribose.

10. A conjugate of claim 8 wherein the 5-[$^{18}$F]fluoro-5-deoxypentose or 3-[$^{18}$F]fluoro-3-deoxypentose is 5-deoxy-5-[$^{18}$F]fluoro-D-ribose or 3-deoxy-3-[$^{18}$F]fluoro-D-ribose.

11. A conjugate of claim 1, wherein the biologically active molecule is conjugated to a 5-[$^{18}$F]fluoro-5-deoxypentose.

12. A method of making a conjugate according to claim 1, comprising reacting the biologically active molecule with a 5-[$^{18}$F]fluoro-5-deoxypentose or a 3-[$^{18}$F]fluoro-3-deoxypentose, wherein the biologically active molecule reacted is derivatised with a linking moiety comprising a nucleophilic amino moiety, wherein the nucleophilic amino moiety is an aminooxy functional group.

13. A method of claim 12 wherein the biologically active molecule is reacted with a 5-[$^{18}$F]fluoro-5-deoxypentose.

14. A composition comprising a conjugate of claim 1 and a pharmaceutically acceptable carrier or diluent.

15. A method of imaging a subject, comprising administering a conjugate of claim 1 to the subject and imaging the distribution of the $^{18}$F-labeled conjugate within the subject.

16. A method of diagnosis of a disease or condition, comprising administering a conjugate of claim 1 to a subject, imaging the distribution of the $^{18}$F-labeled conjugate within the subject, and diagnosing the disease or condition, if present in the subject.

17. A conjugate according to claim 9, wherein the biologically active molecule is conjugated to 5-deoxy-5-[$^{18}$F]fluoro-D-ribose.

18. A method according to claim 12, wherein the biologically active molecule is conjugated to 5-deoxy-5-[$^{18}$F]fluoro-D-ribose.

19. A composition according to claim 14, wherein the biologically active molecule is conjugated to 5-deoxy-5-[$^{18}$F]fluoro-D-ribose.

20. A method of imaging a subject according to claim 15, wherein the biologically active molecule is conjugated to 5-deoxy-5-[$^{18}$F]fluoro-D-ribose.

21. A method of diagnosis of a disease or condition according to claim 16, wherein the biologically active molecule is conjugated to 5-deoxy-5-[$^{18}$F]fluoro-D-ribose.

22. A conjugate of claim 3 wherein the 2-deoxypentose is a 5-[$^{18}$F]fluoro-2,5-dideoxy, 3-[$^{18}$F]fluoro-2,3-dideoxy, 5-[$^{18}$F]fluoro-2,3,5-trideoxy or 3-[$^{18}$F]fluoro-2,3,5-trideoxy pentose, wherein the 2-positions in each of the 5-[$^{18}$F]fluoro-2,5-dideoxy, 3-[$^{18}$F]fluoro-2,3-dideoxy, 5-[$^{18}$F]fluoro-2,3,5-trideoxy and 3-[$^{18}$F]fluoro-2,3,5-trideoxy pentoses, the 3-position in the 5-[$^{18}$F]fluoro-2,3,5-trideoxy pentoses and the 5-position in the 3-[$^{18}$F]fluoro-2,3,5-trideoxy pentoses have a substituent independently selected from the group consisting of hydrogen, halo, alkyl, alkenyl, alkynyl, amino, dialkylamino and alkoxy.

23. A conjugate of claim 8 wherein the biologically active molecule is a peptide.

24. A method of claim 12 wherein the biologically active molecule is a protein or peptide.

25. A method of claim 24 wherein the biologically active molecule is a peptide.

* * * * *